(12) United States Patent
Norman et al.

(10) Patent No.: US 8,710,275 B2
(45) Date of Patent: *Apr. 29, 2014

(54) CATALYSTS AND PROCESS FOR PRODUCING ALDEHYDES

(75) Inventors: David William Norman, Kingsport, TN (US); Joost Nicolaas Hendrik Reek, Amsterdam (NL); Tatiana Renee Marie-Louise Besset, Amsterdam (NL)

(73) Assignee: Eastman Chemical Company, Kingsport, TN (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/484,979

(22) Filed: May 31, 2012

(65) Prior Publication Data

US 2013/0324766 A1 Dec. 5, 2013

(51) Int. Cl.
*C07C 45/50* (2006.01)
*B01J 31/24* (2006.01)

(52) U.S. Cl.
USPC ........... 568/454; 502/102; 502/103; 502/121; 502/123

(58) Field of Classification Search
USPC ................... 568/454; 502/102, 103, 121, 123
See application file for complete search history.

(56) References Cited

U.S. PATENT DOCUMENTS 5,817,884 A * 10/1998 Bahrmann .................... 568/454

FOREIGN PATENT DOCUMENTS

| EP | 1 479 439 A1 | 11/2004 |
|---|---|---|
| EP | 1 888 680 A1 | 2/2008 |
| WO | WO 2008/094222 A2 | 8/2008 |

OTHER PUBLICATIONS

Slagt et al. Encapsulation of Transition Metal Catalysts by Ligand-Template Directed Assemby. Journal of the American Chemical Society, 2004, vol. 126, pp. 1526-1536.*
Kleij et al. Template-Assisted Ligand Encapsulation; the Impact of an Unusual Coordination Geometry on a Supramolecular Pyridylphosphine-Zn (II) porphyrin Assembly. Inorganic Chemistry, 2005, vol. 44, pp. 7696-7698.*
Slagt et al. Fine-Tuning Ligands for Catalysis Using Supramolecular Strategies. European Journal of Inorganic Chemistry, 2007, pp. 4653-4662.*
Adler, Alan D. et al.; "On the Preparation of Metalloporphyrins"; J. inorg. nucl. Chem., vol. 32; 1970; pp. 2443-2445.
Bowen, Richard J. et al.; "Convenient Synthetic Routes to Bidentate and Monodentate 2-, 3- and 4-pyridyl Phosphines: Potentially Useful Ligands for Water-Soluble Complex Catalysts"; Journal of Organometallic Chemistry, vol. 554; 1998; pp. 181-184.
Kamer, Paul C. J. et al.; "Chapter 3 Rhodium Phosphite Catalysts"; Rhodium Catalyzed Hydroformylation; 2000; pp. 35-62.
Kleij, Arjan W. et al.; "Encapsulated Transition Metal Catalysts Comprising Peripheral Zn(II)salen Building Blocks: Template-Controlled Reactivity and Selectivity in Hydroformylation Catalysis"; The Royal Society of Chemistry Communication; 2005; pp. 3661-3663.
Kleij, Arjan W. and Reek, Joost N. H.; "Ligand-Template Directed Assembly: An Efficient Approach for the Supramolecular Encapsulation of Transition-Metal Catalysts"; Chem. Eur. J., vol. 12; 2006; pp. 4218-4227.
Kleij, Arjan W. et al.; "Zn$^{II}$-Salphen Complexes as Versatile Building Blocks for the Construction of Supramolecular Box Assemblies"; Chem. Eur. J, vol. 11; 2005; pp. 4743-4750.
Kleij, Arjan W. et al.; "Template-Assisted Ligand Encapsulation; the Impact of an Unusual Coordination Geometry on a Supramolecular Pyridylphosphine-Zn(II)porphyrin Assembly"; Inorganic Chemistry Communication, vol. 44, No. 22; 2005; pp. 7696-7698.
Kuil, Mark et al.; "High-Precision Catalysts: Regioselective Hydroformylation of Internal Alkenes by Encapsulated Rhodium Complexes"; Journal of American Chemical Society, vol. 128; 2006; pp. 11344-11345.
Meyer, W. H. et al.; "Tri (3-pyridyl) phosphine as amphiphilic ligand in rhodium-catalysed hydroformylation of 1-hexene"; Z. Naturforsch, vol. 62b; 2007; pp. 339-345.
Slagt, Vincent F. et al.; "Assembly of Encapsulated Transition Metal Catalysts"; Angew. Chem. Int. Ed., vol. 40, No. 22; 2001; pp. 4271-4274.
Slagt, Vincent F. et al.; "Encapsulation of Transition Metal Catalysts by Ligand-Template Directed Assembly"; Journal American Chemical Society, vol. 126; 2004; pp. 1526-1536.
Slagt, Vincent et al.; "Fine-Tuning Ligands for Catalysis Using Supramolecular Strategies"; European Journal of Inorganic Chemistry; 2007; pp. 4653-4662.
Van Leeuwen, Piet W. N. M.; "Chapter 1 Introduction to Hydroformylation, Phosphorus Ligands in Homogeneous Catalysis"; Rhodium Catalyzed Hydroformylation; 2000; pp. 1-8.
Van Leeuwen, Piet W. N. M. et al.; "Chapter 4 Phosphines as Ligands, Bite Angle Effects for Diphosphines"; Rhodium Catalyzed Hydroformylation; 2000; pp. 63-105.
Wajda-Hermanowicz, K. et al.; "Rhodium carbonyl complexes of the trans-[RhC1(CO)(PE3)2] type with psyridylphosphines"; Transition Met. Chem., vol. 13; 1988; pp. 101-103.
Co-pending U.S. Appl. No. 13/485,033, filed May 31, 2012; Norman et al.
Co-pending U.S. Appl. No. 13/837,694, filed Mar. 15, 2013; Norman and MacKenzie.
Non-Final Office Action notification date Jul. 16, 2013 received in co-pending U.S. Appl. No. 13/485,033.
Notification of Transmittal of the International Search Report and the Written Opinion of the International Searching Authority, or the Declaration date of mailing Sep. 15, 2013 received in corresponding International Application No. PCT/US2013/042986.
Notification of Transmittal of the International Search Report and the Written Opinion of the International Searching Authority, or the Declaration date of mailing Sep. 16, 2013 received in International Patent Application No. PCT/US2013/042989.
Notification of Transmittal of the International Search Report and the Written Opinion of the International Searching Authority, or the Declaration date of mailing Sep. 16, 2013 received in International Patent Application No. PCT/US2013/042992.

* cited by examiner

*Primary Examiner* — Sikarl Witherspoon
(74) *Attorney, Agent, or Firm* — Ying Yufan Luo

(57) ABSTRACT

Modification of a unique supramolecular assembly of a pyridylphosphine ligand and a metal centered porphyrin complex is shown to give unprecedented selectivities to branched aldehydes via rhodium catalyzed hydroformylation of propylene and 1-octene. Use of magnesium in the porphyrin center provides the highest reported concentrations of iso-butyraldehyde and 2-methyl-octanal.

15 Claims, No Drawings

CATALYSTS AND PROCESS FOR PRODUCING ALDEHYDES

BACKGROUND OF THE INVENTION

Iso-butyraldehyde derivatives are useful solvents and co-monomers in high performance polyesters; however, increasing demands for these materials have created unprecedented challenges for global iso-butyraldehyde production. Hydroformylation, the addition of hydrogen ($H_2$) and carbon monoxide (CO), mixtures of which are known as syngas, to an unsaturated bond is used to produce iso-butyraldehyde from propylene. This process provides a mixture of the linear product, normal-butyraldehyde (N), and the branched, iso-butyraldehyde product (I), with the ratio of normal- to iso-(N:I) typically being greater than or equal to two. The majority of hydroformylation research, particularly within industry, has focused on optimizing the normal aldehyde selectivity while interest in selectively forming the branched aldehyde has only recently emerged. Although an industrially viable process for iso-selective chemistry has yet to be developed, recent academic results have demonstrated highly branched hydroformylation of unsubstituted linear alpha olefins. Selectively hydroformylating at the C2 carbon position of these olefin substrates is quite challenging given that unsubstituted linear alpha olefins bear no discerning electronic or steric features.

To avoid costly separation of linear and branched aldehydes from the product stream it would be preferable to generate branched aldehydes in high concentration. Achieving N:I ratios below 0.6 from 1-octene hydroformylation would therefore be desirable. Achieving less than 1.2 N:I via hydroformylation of an unsubstituted linear alpha-olefin such as propylene would be even more desirable.

BRIEF SUMMARY OF THE INVENTION

According to an embodiment, the invention concerns a process for producing aldehydes, comprising contacting an olefin, with hydrogen and carbon monoxide in the presence of a catalyst composition to produce aldehydes, wherein the catalyst composition comprises a mixture of tris(3-pyridyl) phosphine, a magnesium centered tetraphenylporphyrin coordination complex and a rhodium precursor.

According to another embodiment, the invention concerns a process for producing aldehydes, comprising contacting an olefin, with hydrogen and carbon monoxide in the presence of a catalyst composition to produce aldehydes, wherein the catalyst composition comprises the following structure:

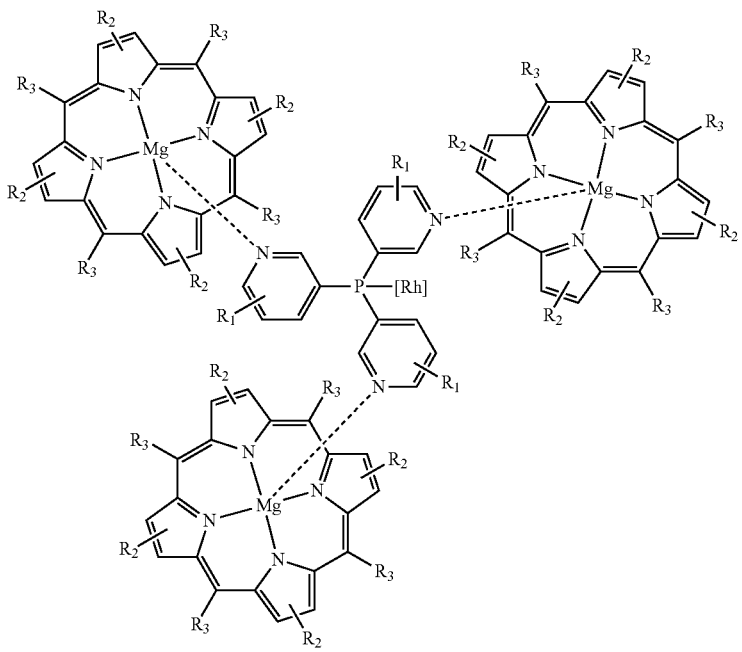

wherein [Rh] is a rhodium(I), rhodium(II) or rhodium(III) metal center; $R_1$ is a hydrogen, alkyl, alkoxy, aryl, aryloxy, halogen, nitro group or other heteroatom positioned at the 2, 4, 5 or 6 carbon position of each pyridyl ring of the phosphine ligand and any combination thereof; $R_2$ is a hydrogen, alkyl, alkoxy, aryl, aryloxy, halogen, nitro group or other heteroatom positioned at the 2 or 3 carbon position of each pyrrole ring of the porphyrin complex and any combination thereof; $R_3$ is a hydrogen or phenyl group that may be substituted with an alkyl, alkoxy, aryl, aryloxy, halogen, nitro group or other heteroatom positioned at the 2, 3, 4, 5 and 6 carbon positions of the phenyl ring and any combination thereof. The phenyl ring may also be displaced by other aromatic hydrocarbons such as naphthalene, anthracene or partially hydrogenated cyclic aromatic compounds such as tetrahydronaphthalene or octahydroanthracene each of which may bear any number of substituents such as alkyl, alkoxy, aryl, aryloxy, halogen, nitro or other heteroatom groups. The pyridyl group of the phosphorus ligand may be displaced by other heterocyclic compounds such as quinoline, hydroquinoline, benzoquinoline, hydroisoquinoline, isoquinoline, hydroisoquinoline, benzoisoquinoline or hydrobenzoisoquinoline each of which may bear any number of substituents such as alkyl, alkoxy, aryl, aryloxy, halogen, nitro or other heteroatom groups.

According to yet another embodiment, the invention concerns a catalyst composition comprising a mixture of tris(3-pyridyl)phosphine, a magnesium centered tetraphenylporphyrin coordination complex and a rhodium precursor.

According to another embodiment, the invention concerns a catalyst composition comprising the following structure:

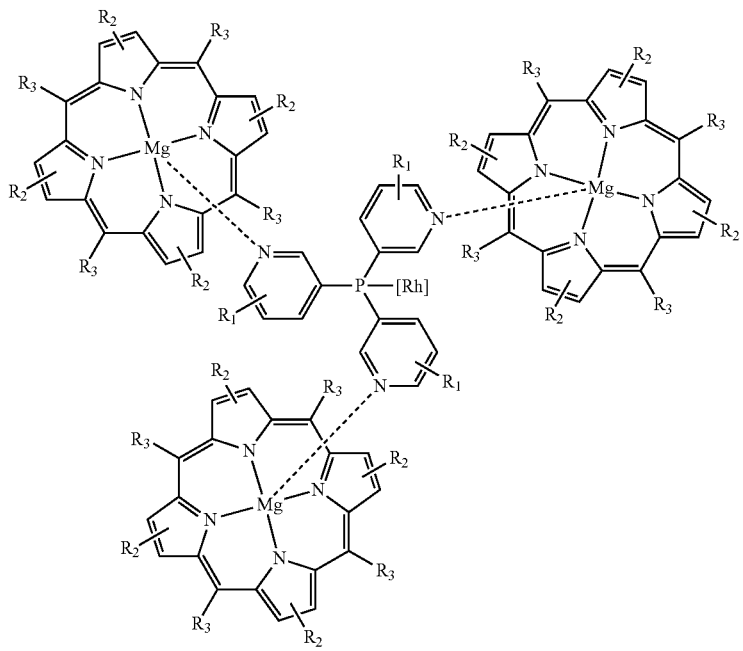

wherein [Rh] is a rhodium(I), rhodium(II) or rhodium(III) metal center; $R_1$ is a hydrogen, an alkyl, alkoxy, aryl, aryloxy, halogen, nitro group or other heteroatom positioned at the 2, 4, 5 or 6 carbon position of each pyridyl ring of the phosphine ligand and any combination thereof; $R_2$ is a hydrogen, an alkyl, alkoxy, aryl, aryloxy, halogen, nitro group or other heteroatom positioned at the 2 or 3 carbon position of each pyrrole ring of the porphyrin complex and any combination thereof; $R_3$ is a hydrogen or phenyl group that may be substituted with an alkyl, alkoxy, aryl, aryloxy, halogen, nitro group or other heteroatom positioned at the 2, 3, 4, 5 and 6 carbon positions of the phenyl ring and any combination thereof. The phenyl ring may also be displaced by other aromatic hydrocarbons such as naphthalene, anthracene or partially hydrogenated cyclic aromatic compounds such as tetrahydronaphthalene or octahydroanthracene, each of which may bear any number of substituents such as alkyl, alkoxy, aryl, aryloxy, halogen, nitro or other heteroatom groups The pyridyl group of the phosphorus ligand may be displaced by other heterocyclic compounds such as quinoline, hydroquinoline, benzoquinoline, hydroisoquinoline, isoquinoline, hydroisoquinoline, benzoisoquinoline or hydrobenzoisoquinoline each of which may bear any number of substituents such as alkyl, alkoxy, aryl, aryloxy, halogen, nitro or other heteroatom groups. According to another embodiment, the invention concerns a method for preparing a catalyst composition comprising contacting a rhodium precursor with tris(3-pyridyl)phosphine and a magnesium centered tetraphenylporphyrin complex in a solvent to form the catalyst composition.

DETAILED DESCRIPTION

Possessing the ability to produce exclusively iso-butyraldehyde at commercially relevant rates would be a significant achievement for industrial hydroformylation processes. Selective synthesis of normal-aldehydes is relatively straightforward given the advances in ligand design over the past several decades. Efforts to produce the branched isomers from unsubstituted linear alpha olefins, however, have met with little success. In other words, methods for producing normal- to iso-aldehyde mixtures in a 1.2:1 to 25:1 ratio via rhodium catalysis are well established but industrial technologies for obtaining N:I ratios below 1.2:1 remain in their infancy. For purposes of this invention, N refers to normal (or linear) aldehydes which arise from hydroformylation of the C1 carbon of the olefin substrate and I refers to non-linear aldehydes which arise from hydroformylation of the C2 carbon of the olefin substrate. Moreover, for purposes of the invention, the terminology olefin, olefin substrate and substrate are used interchangeably.

According to an embodiment, the present invention shows that a modification of a ligand system affords unprecedented branched aldehyde selectivity from the hydroformylation of linear alpha-olefins. The "ligand system" is defined as a mixture of tris(3-pyridyl)phosphine (hereafter referred to as "PPy3" or "phosphine ligand" or "ligand" or "phosphine" or "pyridylphosphine") and a metal centered 5, 10, 15, 20-tetraphenylporphyrin coordination complex (hereafter referred to as "porphyrin complex" or "TPP-M" where M is the metal coordinated by the porphyrin) and a rhodium precursor. Moreover, the "catalyst composition" according to the present invention is a composition comprising PPy3, TPP-magnesium (or TTP-Mg) and a rhodium precursor. Hence, according to an embodiment, a catalyst composition according to the present invention has the following structure:

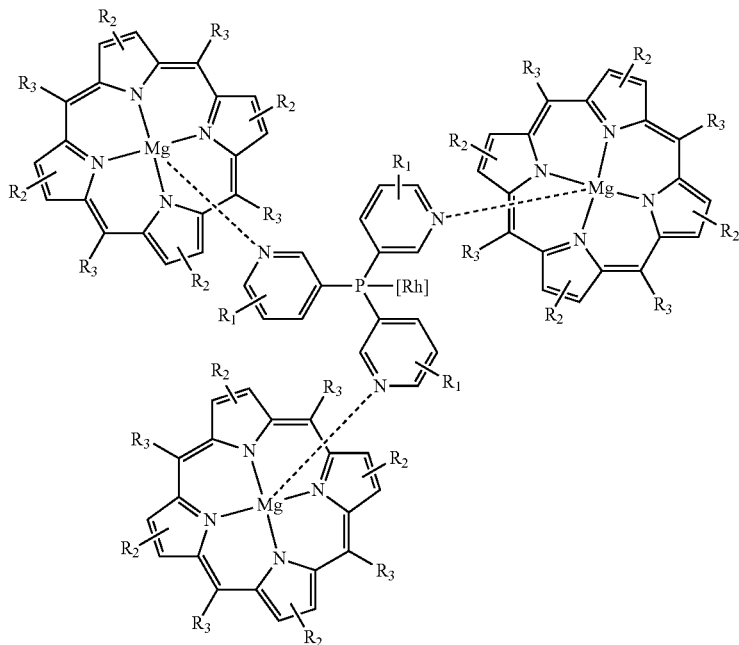

wherein [Rh] is a rhodium(I), rhodium(II) or rhodium(III) metal center; $R_1$ is a hydrogen, an alkyl, alkoxy, aryl, aryloxy, halogen, nitro group or other heteroatom positioned at the 2, 4, 5 or 6 carbon position of each pyridyl ring of the phosphine ligand and any combination thereof; $R_2$ is a hydrogen, an alkyl, alkoxy, aryl, aryloxy, halogen, nitro group or other heteroatom positioned at the 2 or 3 carbon position of each pyrrole ring of the porphyrin complex and any combination thereof; $R_3$ is a hydrogen or phenyl group that may be substituted with an alkyl, alkoxy, aryl, aryloxy, halogen, nitro group or other heteroatom positioned at the 2, 3, 4, 5 and 6 carbon positions of the phenyl ring and any combination thereof. The phenyl ring may also be displaced by other aromatic hydrocarbons such as naphthalene, anthracene or partially hydrogenated cyclic aromatic compounds such as tetrahydronaphthalene or octahydroanthracene, each of which may bear any number of substituents such as alkyl, alkoxy, aryl, aryloxy, halogen, nitro or other heteroatom groups. The pyridyl group of the phosphorus ligand may be displaced by other heterocyclic compounds such as quinoline, hydroquinoline, benzoquinoline, hydroisoquinoline, isoquinoline, hydroisoquinoline, benzoisoquinoline or hydrobenzoisoquinoline each of which may bear any number of substituents such as alkyl, alkoxy, aryl, aryloxy, halogen, nitro or other heteroatom groups.

According to an embodiment, the rhodium precursor can be any rhodium containing complex or salt bearing spectator ligands such as, but not limited to, acetylacetonatobis(cyclooctene)rhodium(I); acetylacetonatobis(ethylene)rhodium (I); acetylacetonato(1,5-cyclooctadiene)rhodium(I); bis(1,5-cycloocta-diene)rhodium(I)tetrafluoroborate; bis(1,5-cyclooctadiene)rhodium(I) trifluoromethanesulfonate; bis (norbornadiene)rhodium(I)tetrafluoroborate; chlorobis (cyclooctene)rhodium(I)dimer; chlorobis(ethylene)rhodium (I)dimer; chloro(1,5-cyclooctadiene)rhodium(I)dimer; chlorodicarbonylrhodium(I)dimer; chloronorbornadiene rhodium(I)dimer; dicarbonylacetylacetonato rhodium(I); rhodium(II)acetate dimer; rhodium(III)acetylacetonate; rhodium(III)bromide; rhodium(III)chloride; rhodium(III)iodide; rhodium(II)nitrate; rhodium(II octanoate dimer; rhodium(II)trifluoroacetate dimer; tetrarhodium dodecacarbonyl; di-rhodium tetraacetate dehydrate; rhodium(II)acetate; rhodium(II)isobutyrate; rhodium(II)2-ethylhexanoate; rhodium (II)benzoate and rhodium(II)octanoate. Also, rhodium carbonyl species such as $Rh_4$ $(CO)_{12}$ and $Rh_6(CO)_{16}$ may be suitable rhodium feeds. Additionally, rhodium organophosphine complexes such as tris(triphenylphosphine)rhodium carbonyl hydride may be used when the phosphine moieties of the complex fed are easily displaced by the tris(3-pyridyl) phosphine ligand of the present invention.

According to an embodiment, the catalyst can be prepared by combining a rhodium precursor with tris(3-pyridyl)phosphine and the magnesium centered tetraphenylporphyrin complex in a solvent. Examples of solvents include, but are not limited to, alkanes, cycloalkanes, alkenes, cycloalkenes, carbocyclic aromatic compounds, alcohols, esters, ketones, acetals, ethers and water. Specific examples of such solvents include alkane and cycloalkanes such as dodecane, decalin, octane, iso-octane mixtures, cyclohexane, cyclooctane, cyclododecane, methylcyclohexane; aromatic hydrocarbons such as benzene, toluene, xylene isomers, tetralin, cumene, alkyl-substituted aromatic compounds such as the isomers of diisopropylbenzene, triisopropylbenzene and tert-butylbenzene; crude hydrocarbon mixtures such as naphtha, mineral oils and kerosene; high-boiling esters such as 2,2,4-trimethyl-1,3-pentanediol diisobutyrate. The aldehyde product of the hydroformylation process also may be used. The main criteria for the solvent is that it dissolves the catalyst and olefin substrate and does not act as a poison to the catalyst. Examples of solvents for the production of volatile aldehydes, e.g., the butyraldehydes, are those that are sufficiently high boiling to remain, for the most part, in a gas sparged reactor. Solvents and solvent combinations that are preferred for use in the production of less volatile and non-volatile aldehyde products include 1-methyl-2-pyrrolidinone, dimethylformamide, perfluorinated solvents such as perfluorokerosene, sulfolane, water, and high boiling hydrocarbon liquids as well as combinations of these solvents.

An embodiment of the invention described herein demonstrates the effect of substituting the zinc center of the porphyrin complex with magnesium. It has been surprisingly discovered that this substitution of zinc for magnesium affords a catalyst composition capable of producing as much as 74% iso-aldehyde (N:I=0.35) from 1-octene hydroformylation when performed at 19° C. and with 21.7 bara (bar absolute) (300 psig) of 1:1 $H_2$:CO. The same reaction performed with the zinc containing catalyst composition gives 62% iso-aldehyde (N:I=0.61).

The magnesium effect comes as a surprise since other porphyrin complexes with metal centers such as oxovanadium, cobalt, copper and nickel afford ligand systems that give only 25% to 50% iso-aldehyde (N:I=1 to 3) under otherwise identical reaction conditions.

The magnesium effect is notable for olefin substrates. For example, the ratio of iso-butyraldehyde to normal-butyraldehyde is 0.6 (63% branched product) when the magnesium porphyrin complex is used at 21.7 bara (300 psig) and 19° C. In comparison, the zinc system affords an N:I ratio of 1.0 (50% branched product) under otherwise identical reaction conditions.

Increasing the 1:1 $H_2$:CO pressure to 83.7 bara (1,200 psig) during 1-octene hydroformylation at 19° C. significantly improves the iso-selectivity in both the magnesium and zinc porphyrin systems. Interestingly, however, is the observation that the magnesium system again forms more branched product than the zinc congener (N:I=0.25 vs. 0.47). The zinc system gives 68% 2-methyl-octanal whereas the magnesium analogue affords 80%, which is an unprecedented selectivity for this branched aldehyde.

According to an embodiment, the present invention concerns a process for producing aldehydes, such as branched aldehydes, comprising contacting an olefin, with hydrogen and carbon monoxide, under hydroformylation conditions to produce aldehydes, in the presence of a catalyst composition comprising tris(3-pyridyl)phosphine, a magnesium centered tetraphenylporphyrin coordination complex and a rhodium precursor.

According to another embodiment, the invention concerns a process for producing aldehydes, such as branched aldehydes, comprising contacting an olefin, with hydrogen and carbon monoxide, under hydroformylation conditions to produce aldehydes, in the presence of a catalyst composition comprising the following structure:

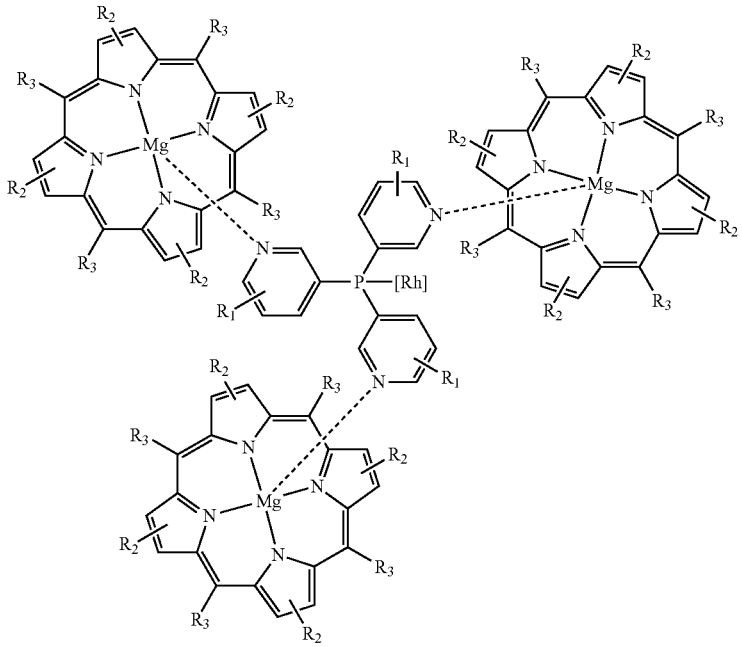

wherein [Rh] is a rhodium(I), rhodium(II) or rhodium(III) metal center; $R_1$ is a hydrogen, an alkyl, alkoxy, aryl, aryloxy, halogen, nitro group or other heteroatom positioned at the 2, 4, 5 or 6 carbon position of each pyridyl ring of the phosphine ligand and any combination thereof; $R_2$ is a hydrogen, an alkyl, alkoxy, aryl, aryloxy, halogen, nitro group or other heteroatom positioned at the 2 or 3 carbon position of each pyrrole ring of the porphyrin complex and any combination thereof; $R_3$ is a hydrogen or phenyl group that may be substituted with an alkyl, alkoxy, aryl, aryloxy, halogen, nitro group or other heteroatom positioned at the 2, 3, 4, 5 and 6 carbon positions of the phenyl ring and any combination thereof. The phenyl ring may also be displaced by other aromatic hydrocarbons such as naphthalene, anthracene or partially hydrogenated cyclic aromatic compounds such as tetrahydronaphthalene or octahydroanthracene, each of which may bear any number of substituents such as alkyl, alkoxy, aryl, aryloxy, halogen, nitro or other heteroatom groups. The pyridyl group of the phosphorus ligand may be displaced by other heterocyclic compounds such as quinoline, hydroquinoline, benzoquinoline, hydroisoquinoline, isoquinoline, hydroisoquinoline, benzoisoquinoline or hydrobenzoisoquinoline each of which may bear any number of substituents such as alkyl, alkoxy, aryl, aryloxy, halogen, nitro or other heteroatom groups.

According to an embodiment, the mole ratio of metal porphyrin complex to tris(3-pyridyl)phosphine can be from about 1,000:1 to 3:1 or from about 500:1 to about 100:1 or even from about 10:1 to about 3:1. The mole ratio of tris(3-pyridyl)phosphine ligand to rhodium can be from about 1,000:1 to about 1:1 or from about 500:1 to about 100:1 or even from about 10:1 to about 1:1. The mole ratio of the olefin substrate to rhodium can be from about 100,000:1 to about 10:1 or from about 10,000:1 to about 100:1 or even from about 5,000:1 to about 1,000:1.

The pressure of the reaction can be from about 345.7 bara (5,000 psig) to about 1.07 bara (1 psig) or from about 69.9 bara (1000 psig) to about 7.9 bara (100 psig) or even from about 35.5 bara (500 psig) to about 14.8 bara (200 psig). The temperature of the reactor can be from about 500° C. to about 0° C. or from about 100° C. to 50° C. or even from about 90° C. to about 70° C. The molar ratio of carbon monoxide to hydrogen can be from about 100:1 to about 0.1:1 or from about 50:1 to about 10:1 or even from 4:1 to about 1:1. The rate of reaction, or turnover frequency, can be from about 1,000,000 $h^{-1}$ to about 100 $h^{-1}$ or from about 100,000 $h^{-1}$ to about 1000 $h^{-1}$ or even from about 10,000 $h^{-1}$ to about 3,000 $h^{-1}$. The N:I ratio of normal-aldehyde product relative to iso-aldehyde product can be from about 2.0:1 to about 0.01:1 or from about 0.6:1 to about 0.1:1 or from about 0.4:1 to about 0.25:1.

According to an embodiment, the olefin substrates used in these hydroformylation reactions can be aliphatic, including ethylenically-unsaturated, low molecular weight polymers, alicyclic, aromatic and heterocyclic mono-, di- and triolefins containing up to about 40 carbon atoms. Examples of the aliphatic olefins that may be utilized in the process include straight- and branched-chain, unsubstituted and substituted, aliphatic mono-alpha-olefins containing up to about 20 carbon atoms. Examples of the groups that may be present on the substituted mono-alpha-olefins include hydroxy; alkoxy including ethers and acetals; alkanoyloxy such as acetoxy; amino including substituted amino; carboxy; alkoxycarbonyl; carboxamide; keto; cyano; and the like. Preferred aliphatic mono-alpha-olefins have the general formulas: $H_2C=CH—R_4$ and $H_2C=CH—R_5—R_6$ wherein $R_4$ is hydrogen or straight- or branched-chain alkyl of up to about 8 carbon atoms; $R_5$ is straight- or branched-chain alkylene of up to about 18 carbon atoms; and $R_6$ is hydroxy, alkoxy of up to about 4 carbon atoms, alkanoyloxy of up to about 4 carbon atoms, carboxyl or alkoxycarbonyl of 2 to about 10 carbon atoms. Specific examples of the aliphatic mono-alpha-olefins include ethylene, propylene, 1-butene, 1-pentene, 1-hexene, 1-heptene, 1-octene, 1-nonene, 1-decene, 1-undecene, 1-dodecene, allyl alcohol and 3-acetoxy-1-propene. The aliphatic, di-olefins may contain up to about 40 carbon atoms. Preferred aliphatic, di-olefins have the general formula: $H_2C=CH—R_7—CH=CH_2$ wherein $R_7$ is straight- or branched-chain alkylene having 1 to about 18 carbon atoms. The cyclic olefins which may be used in the hydroformylation process of the present invention may be cycloalkenes, e.g., cyclohexene, 1,5-cyclooctadiene, and cyclodecatriene, and from various vinyl-substituted cycloalkanes, cycloalkenes, heterocyclic and aromatic compounds. Examples of such cyclic olefins include 4-vinylcyclohexene, 1,3-cyclohexadiene, 4-cyclohexene-carboxylic acid, methyl 4-cyclohexene-carboxylic acid, 1,4-cyclooctadiene and 1,5,9-cyclododecatriene.

According to an embodiment, the porphyrin complex is comprised of at least a 5,10,15,20-tetraphenylporphyrin moiety bound to a magnesium ion. The tetraphenylporphyrin fragment may bear functionalized phenyl rings in order to change the steric and electronic properties of the catalyst. For example, the phenyl groups of the porphyrin moiety may be substituted with one or more methyl groups, methoxy groups or nitro groups at the 2, 3, 4, 5 and 6 carbon positions of the phenyl ring. The phenyl ring may also be displaced by other aromatic cyclic hydrocarbons such as naphthalene, anthracene or partially hydrogenated cyclic aromatic compounds such as tetrahydronaphthalene or octahydroanthracene.

Examples of suitable reactor types include, but are not limited to, stirred tank, continuous stirred tank, and tubular reactors. Any of the known hydroformylation reactor designs or configurations may be used for the hydroformylation reaction to produce the aldehyde hydroformylation product. For example, the process may be conducted in a batchwise manner in an autoclave by contacting the substrate olefin with syngas in the presence of the catalyst compositions described herein. It will be apparent to those skilled in the art that other reactor schemes may be used with this invention. For example, the hydroformylation reaction can be conducted in a plurality of reaction zones, in series, in parallel, or it may be conducted batchwise or continuously in a tubular plug flow reaction zone or series of such zones with recycle of unconsumed feed substrate materials if required. The reaction steps may be carried out by the incremental addition of one of the feed substrate materials to the other. Also, the reaction steps can be combined by the joint addition of the feed substrate materials.

EXAMPLES

This invention can be further illustrated by the following examples of preferred embodiments thereof, although it will be understood that these examples are included merely for purposes of illustration and are not intended to limit the scope of the invention unless otherwise specifically indicated.

Abbreviations:

TON=Turnover number; TOF=Turnover frequency; N=normal-aldehyde; I=iso-aldehyde; acac=acetylacetonate; TPP=Tetraphenylporphyrin (5,10,15,20-Tetraphenyl-21H, 23H-porphine); GC=Gas chromatography; S/Rh=Substrate/rhodium, L/Rh=Ligand/rhodium, TPP/L=Tetraphenylporphyrin/ligand, M=the metal bound in the porphyrin complex; Isom.=percent isomerization.

General:

The rhodium precursor, $Rh(acac)(CO)_2$, and 1-octene were purchased from commercial suppliers. Propylene (propene) was delivered quantitatively to the reactors by a Brooks Quantim mass flow controller. The metal porphyrin complexes, denoted as TPP-M, were either purchased from commercial suppliers or prepared according to known methods. All chemical manipulations, unless otherwise stated, were carried out under an inert atmosphere. The ligand used in the examples described below is tris(3-pyridyl)phosphine, prepared via modifications of published procedures:

A solution of 1.6 mol/L butyl lithium in hexanes (65 mL, 104 mmol) and TMEDA (14.2 mL, 94.5 mmol) was stirred in a dry flask under nitrogen for 15 minutes. The mixture was cooled to −72° C. and cold dry diethyl ether (300 mL) was added. The solution was then cooled to −115° C. 3-Bromopyridine (9.7 mL, 100.3 mmol) in 50 mL diethyl ether was added dropwise over 30 minutes keeping the temperature below −100° C. This was followed by the addition of PCl$_3$ (1.68 mL, 19.3 mmol) and after 30 minutes of stirring, a second aliquot of PCl$_3$ (0.72 mL, 1.14 mmol). The mixture was stirred for 2 hours at −100° C. and left to warm to room temperature overnight. The mixture was extracted with degassed water (4×300 mL) and the combined aqueous layers were washed with chloroform (3×400 mL). The combined organic layers were dried over MgSO$_4$ and concentrated to afford 6.65 g of a caramel-colored oil. The oil was purified by silica gel chromatography (column pre-treated with 5% triethylamine/heptane) using 0.5% MeOH/0.5% TEA/heptane to afford 2.9 g (39.6% yield) of a white solid. $^{31}$P NMR (300 MHz, CDCl$_3$) δ-24.46. $^1$H NMR (300 MHz, CDCl$_3$) δ 8.64 (dt, J=4.8, 1.5 Hz, 3H), 8.61-8.52 (m, 3H), 7.71-7.52 (m, 3H), 7.42-7.29 (m, 3H).

Calculations:

Percent conversion=[(amount of octene isomers+ amount of products)/(amount of 1-octene fed+ amount of octene isomers+amount of products)]× 100%

Percent isomerization=[(amount of internal octenes+ amount of 2-propylhexanal+amount of 2-ethylheptanal)/(amount of 2-methyl-octanal+amount of nonanal+amount of internal octenes+amount of 2-propylhexanal+amount of 2-ethylheptanal)]×100%

Percent iso-aldehyde=[(amount iso-aldehyde)/ (amount iso-aldehyde+amount normal-aldehyde)]×100%

Percent normal-aldehyde=[(amount normal-aldehyde)/(amount normal-aldehyde+amount iso-aldehyde)]×100%

TON=[(moles of desired aldehyde produced)/(moles of Rh(acac)(CO)$_2$)]

TOF=[(moles of desired aldehyde produced)/(moles of Rh(acac)(CO)$_2$)]/hour

Example 1

Effect of Using a Magnesium Porphyrin Complex with the Tris(3-Pyridyl)Phosphine Rhodium System at 19° C. with 1-Octene as Substrate The hydroformylation reaction in this example was carried out by first dissolving Rh(acac)(CO)$_2$ (7.6 mg, 0.03 mmol) in toluene (45 mL) followed by addition of tris(3-pyridyl)phosphine (17.5 mg, 0.066 mmol) then addition of the tetraphenylporphyrin magnesium complex (125 mg, 0.2 mmol). The solution was then degassed by argon bubbling followed by addition of 1-octene (1.37 g, 12.2 mmol) and a decane internal standard, both via syringe. The solution was then charged to an autoclave which was then pressurized and vented three times with nitrogen. Stirring was set to 1,000 rpm, the reactor temperature maintained at 19° C. and 21.7 bara (300 psig) of a 1:1 CO:H$_2$ gas mixture added. After eighteen hours, the autoclave was vented and the product analyzed by gas chromatography. The results are summarized in Table 1.

This example demonstrates that the magnesium porphyrin complex, when used with the pyridylphosphine ligand and a rhodium precursor, affords an N:I ratio of 0.35, which equates to 74% iso-aldehyde concentration.

Examples 2 to 6

Effect of Using Other Metal Porphyrin Complexes with the Tris(3-Pyridyl)Phosphine Rhodium System at 19° C. with 1-Octene as Substrate These Examples were carried out as described in Example 1 except that different metal porphyrin complexes were used; the results are summarized in Table 1. Consistent with the prior art, the zinc porphyrin system affords an N:I ratio of 0.61 (62% iso-aldehyde). Other porphyrin metal complexes, however, have undesirable and unpredictable effects on the N:I selectivity.

TABLE 1

| Example | Press. (bara) | Time (h) | Temp. (° C.) | Substrate | M | S/Rh | L/Rh | TPP/L | Conv. | N:I | iso- | Isom. |
|---|---|---|---|---|---|---|---|---|---|---|---|---|
| Ex. 1 | 21.7 | 18 | 19 | 1-Octene | Mg | 415 | 2.2 | 3.0 | 63% | 0.35 | 74% | 0% |
| Ex. 2 | 21.7 | 18 | 19 | 1-Octene | Zn | 377 | 2.1 | 2.9 | 98% | 0.61 | 62% | 0% |
| Ex. 3 | 21.7 | 18 | 19 | 1-Octene | V(O) | 415 | 2.1 | 2.9 | 40% | 3.0 | 25% | 0% |
| Ex. 4 | 21.7 | 18 | 19 | 1-Octene | Co | 408 | 2.4 | 2.7 | 63% | 1.01 | 50% | 0% |
| Ex. 5 | 21.7 | 18 | 19 | 1-Octene | Cu | 392 | 2.4 | 2.6 | 44% | 2.94 | 25% | 0% |
| Ex. 6 | 21.7 | 18 | 19 | 1-Octene | Ni | 404 | 2.2 | 5.5 | 41% | 2.98 | 35% | 0% |

Examples 7 and 8

Effect of Using a Metal Porphyrin Complex with the Tris(3-Pyridyl)Phosphine Rhodium System at 80° C. with 1-Octene as Substrate The hydroformylation reactions in these examples were carried out as described in Example 1 except that the autoclave was heated to 80° C. prior to the pressurization step. After one hour, the autoclave was vented then cooled and the product analyzed by gas chromatography. The results are summarized in Table 2. These examples demonstrate that both the TPP-zinc and TPP-magnesium systems provide an N:I ratio between 1.5 and 1.6 at 80° C. (~40% iso-aldehyde). This confirms that the magnesium system is at least as effective as the zinc at elevated temperature. Indeed, as reported previously, the N:I selectivity under these conditions is about 3.0 when the hydroformylation is performed in the absence of a porphyrin complex.

TABLE 2

| Example | Press. (bara) | Time (h) | Temp. (° C.) | Substrate | M | S/Rh | L/Rh | TPP/L | Conv. | N:I | iso- | Isom. |
|---|---|---|---|---|---|---|---|---|---|---|---|---|
| Ex. 7 | 21.7 | 1 | 80 | 1-Octene | Mg | 383 | 2.0 | 3.3 | 99% | 1.52 | 40% | 8% |
| Ex. 8 | 21.7 | 1 | 80 | 1-Octene | Zn | 413 | 2.5 | 2.9 | 99% | 1.58 | 39% | 5% |

Examples 9 and 10

Effect of Using a Metal Porphyrin Complex with the Tris(3-Pyridyl)Phosphine Rhodium System at 19° C. with Propene as the Substrate The hydroformylation reactions in these examples were carried out as described in Example 1 except that the substrate used was propylene (propene). The results are summarized in Table 3. These examples clearly show that the TPP-magnesium system affords a higher iso-aldehyde concentration than the zinc congener at 19° C. The magnesium based catalyst affords an N:I ratio of 0.6 (63% iso-butyraldehyde) while the zinc system gives an N:I of 1.0 (50% iso-butyraldehyde). Consistent with the 1-octene results, this branched aldehyde selectivity is the highest reported for the rhodium catalyzed hydroformylation of propylene.

TABLE 3

| Example | Press. (bara) | Time (h) | Temp. (° C.) | Substrate | M | S/Rh | L/Rh | TPP/L | Conv. | N:I | iso- | Isom. |
|---|---|---|---|---|---|---|---|---|---|---|---|---|
| Ex. 9 | 21.7 | 18 | 19 | Propene | Mg | 401 | 2.1 | 3.0 | 85% | 0.6 | 63% | n/a |
| Ex. 10 | 21.7 | 18 | 19 | Propene | Zn | 396 | 2.2 | 2.9 | 73% | 1.0 | 50% | n/a |

Examples 11 and 12

Effect of Using a Metal Porphyrin Complex with the Tris(3-Pyridyl)Phosphine Rhodium System at 80° C. with Propene as the Substrate The hydroformylation reactions in these examples were carried out as described in Example 7 except that the substrate used was propylene. The amount of ligand used in Example 12 was four times the standard amount. The results are summarized in Table 4. These examples demonstrate that there is little difference in iso-butyraldehyde selectivity when the magnesium or zinc TPP systems are employed at 80° C. and when propene is the substrate. This is consistent with the 1-octene experiments under the same reactor conditions.

TABLE 4

| Example | Press. (bara) | Time (h) | Temp. (° C.) | Substrate | M | S/Rh | L/Rh | TPP/L | Conv. | N:I | iso- | Isom. |
|---|---|---|---|---|---|---|---|---|---|---|---|---|
| Ex. 11 | 21.7 | 1 | 80 | Propene | Mg | 358 | 2.2 | 3.0 | 100% | 1.63 | 38% | n/a |
| Ex. 12 | 21.7 | 1 | 80 | Propene | Zn | 374 | 8.0 | 2.9 | 100% | 1.58 | 39% | n/a |

Examples 13 and 14

Effect of Increased Equimolar Syngas Pressure Using a Metal Porphyrin Complex with the Tris(3-Pyridyl)Phosphine Rhodium System at 19° C. with 1-Octene as the Substrate The hydroformylation reactions in these examples were carried out as described in Example 1 except that the 1:1 $CO:H_2$ pressure was 83.7 bara (1200 psig). The results are summarized in Table 5. In both examples the increased reactor pressure decreased the N:I ratio such that the zinc system gave an N:I of 0.47 (68% iso-aldehyde) and the magnesium system gave an N:I of 0.25 (80% iso-aldehyde). The selectivity imparted by the magnesium system at elevated pressure is the highest reported for rhodium catalyzed hydroformylation of unsubstituted linear alpha olefins and is unexpected since increasing syngas pressure generally has unpredictable effects in many hydroformylation catalyst systems.

TABLE 5

| Example | Press. (bara) | Time (h) | Temp. (° C.) | Substrate | M | S/Rh | L/Rh | TPP/L | Conv. | N:I | iso- | Isom. |
|---|---|---|---|---|---|---|---|---|---|---|---|---|
| Ex. 13 | 83.7 | 18 | 19 | 1-Octene | Mg | 407 | 2.1 | 3.0 | 51% | 0.25 | 80% | 0% |
| EX. 14 | 83.7 | 18 | 19 | 1-Octene | Zn | 357 | 2.0 | 2.9 | 100% | 0.47 | 68% | 0% |

Examples 15 and 16

Effect of Increased Equimolar Syngas Pressure Using a Metal Porphyrin Complex with the Tris(3-Pyridyl)Phosphine Rhodium System at 80° C. with 1-Octene as the Substrate The hydroformylation reaction in these examples was carried out as described in Example 7 except that the 1:1 CO:$H_2$ pressure was 83.7 bara (1200 psig). The results are summarized in Table 6. Upon comparison with Example 7, Example 15 demonstrates that the increased reactor pressure decreased the N:I ratio to 1.15 (47% iso-aldehyde) from 1.52 (40% iso-aldehyde) when the magnesium system was used at elevated temperature. The zinc system described in Example 16, on the other hand, does not show any enhanced iso-aldehyde selectivity under these conditions.

TABLE 6

| Example | Press. (bara) | Time (h) | Temp. (° C.) | Substrate | M | S/Rh | L/Rh | TPP/L | Conv. | N:I | iso- | Isom. |
|---|---|---|---|---|---|---|---|---|---|---|---|---|
| Ex. 15 | 83.7 | 1 | 80 | 1-Octene | Mg | 382 | 2.2 | 2.9 | 99% | 1.15 | 47% | 6% |
| Ex. 16 | 83.7 | 1 | 80 | 1-Octene | Zn | 439 | 2.2 | 2.8 | 100% | 1.58 | 39% | 5% |

The invention has been described in detail with particular reference to preferred embodiments thereof, but it will be understood that variations and modifications can be effected within the spirit and scope of the invention.

We claim:

1. A process for producing aldehydes, comprising contacting an olefin, with hydrogen and carbon monoxide in the presence of a catalyst composition to produce said aldehydes, wherein the catalyst composition comprises:

a mixture of tris(3-pyridyl)phosphine, a magnesium centered tetraphenylporphyrin coordination complex and a rhodium precursor.

2. A process according to claim 1, wherein the aldehydes are produced in an N:I ratio of from about 2.0:1 to about 0.01:1.

3. A process according to claim 2, wherein the N:I ratio is from about 0.6:1 to about 0.11:1.

4. The process according to claim 3, wherein the N:I ratio is from about 0.4:1 to about 0.25:1.

5. The process according to claim 1, wherein the olefin is an unsubstituted linear alpha-olefin.

6. The process according to claim 5, wherein the olefin is propylene, 1-butene, 1-pentene, 1-hexene, 1-heptene, 1-octene, 1-nonene, 1-decene, 1-undecene, 1-dodecene or mixtures thereof.

7. The process according to claim 1, wherein a mole ratio of magnesium centered tetraphenylporphyrin coordination complex to tris(3-pyridyl)phosphine is from about 1,000:1 to 3:1.

8. The process according to claim 1, wherein a mole ratio of tris(3-pyridyl)phosphine ligand to rhodium precursor is from about 1000:1 to about 1:1.

9. The process according to claim 1, wherein a mole ratio of olefin to rhodium precursor is from about 100,000:1 to about 10:1.

10. The process according to claim 1, wherein a ratio of carbon monoxide to hydrogen can be from about 100:1 to about 0.1:1.

11. A process for producing aldehydes, comprising contacting an olefin, with hydrogen and carbon monoxide in the presence of a catalyst composition to produce aldehydes, wherein the catalyst composition comprises the following structure:

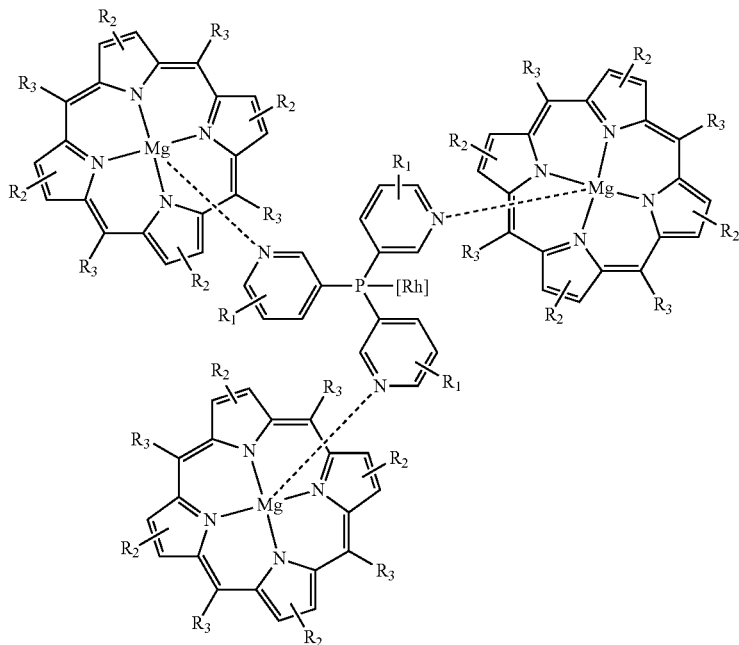

wherein Rh is a rhodium(I), rhodium(II) or rhodium(III) metal center;

$R_1$ is a hydrogen, alkyl, alkoxy, aryl, aryloxy, halogen, nitro group or other heteroatom positioned at a 2, 4, 5 or 6 carbon of each pyridyl ring of the phosphine or any combination thereof;

$R_2$ is a hydrogen, alkyl, alkoxy, aryl, aryloxy, halogen, nitro group or other heteroatom positioned at a 2 or 3 carbon position of each pyrrole ring of the porphyrin complex and any combination thereof; and $R_3$ is a hydrogen or phenyl group that may be substituted with an alkyl, alkoxy, aryl, aryloxy, halogen, nitro group or other heteroatom positioned at a 2, 3, 4, 5 and 6 carbon positions of the phenyl ring and any combination thereof.

12. A catalyst composition comprising tris(3-pyridyl) phosphine, a magnesium centered tetraphenylporphyrin coordination complex and a rhodium precursor.

13. A catalyst composition comprising the following structure:

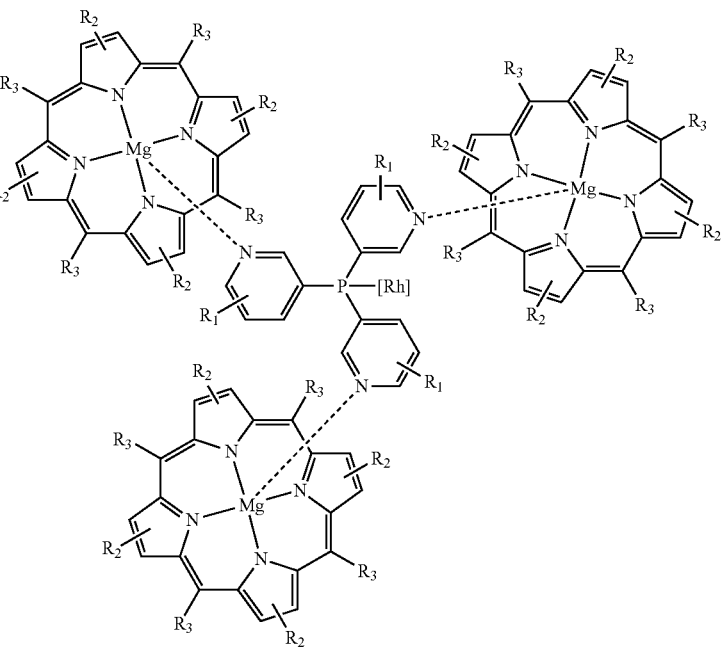

wherein Rh is a rhodium(I), rhodium(II) or rhodium(III) metal center;

$R_1$ is a hydrogen, alkyl, alkoxy, aryl, aryloxy, halogen, nitro group or other heteroatom positioned at a 2, 4, 5 or 6 carbon of each pyridyl ring of the phosphine or any combination thereof;

$R_2$ is a hydrogen, alkyl, alkoxy, aryl, aryloxy, halogen, nitro group or other heteroatom positioned at a 2 or 3 carbon position of each pyrrole ring of the porphyrin complex and any combination thereof; and $R_3$ is a hydrogen or phenyl group that may be substituted with an alkyl, alkoxy, aryl, aryloxy, halogen, nitro group or other heteroatom positioned at a 2, 3, 4, 5 and 6 carbon positions of the phenyl ring and any combination thereof.

14. A method for preparing a catalyst composition comprising contacting a rhodium precursor with tris(3-pyridyl)phosphine and a magnesium centered tetraphenylporphyrin complex in a solvent to form the catalyst composition.

15. The method according to claim 14, wherein the solvent is a benzene, a toluene, a xylene, a pentane, a hexane, a heptane, an octane, a nonane, an ethyl acetate, a dichloromethane, a diethyl ether or mixtures thereof.

* * * * *